US011201355B2

(12) United States Patent
Iida et al.

(10) Patent No.: US 11,201,355 B2
(45) Date of Patent: Dec. 14, 2021

(54) NONAQUEOUS ELECTROLYTE SECONDARY BATTERY

(71) Applicant: Panasonic Corporation, Kadoma (JP)

(72) Inventors: Kazuhiro Iida, Tokyo (JP); Takanobu Chiga, Osaka (JP); Naoya Morisawa, Hyogo (JP); Atsushi Fukui, Hyogo (JP)

(73) Assignee: PANASONIC CORPORATION, Kadoma (JP)

( * ) Notice: Subject to any disclaimer, the term of this patent is extended or adjusted under 35 U.S.C. 154(b) by 146 days.

(21) Appl. No.: 16/523,365

(22) Filed: Jul. 26, 2019

(65) Prior Publication Data

US 2019/0348716 A1 Nov. 14, 2019

Related U.S. Application Data

(63) Continuation of application No. PCT/JP2017/043909, filed on Dec. 7, 2017.

(30) Foreign Application Priority Data

Jan. 30, 2017 (JP) .............................. JP2017-014672

(51) Int. Cl.
*H01M 10/0569* (2010.01)
*H01M 10/0567* (2010.01)
*H01M 10/0525* (2010.01)
*H01M 4/525* (2010.01)
*C07C 49/10* (2006.01)
*C07C 49/205* (2006.01)

(52) U.S. Cl.
CPC ......... *H01M 10/0569* (2013.01); *C07C 49/10* (2013.01); *C07C 49/205* (2013.01); *H01M 4/525* (2013.01); *H01M 10/0525* (2013.01); *H01M 10/0567* (2013.01); *H01M 2300/0034* (2013.01)

(58) Field of Classification Search
CPC .... H01M 4/5825; H01M 4/485; H01M 4/366; H01M 10/052; H01M 4/525; H01M 10/0525; H01M 10/0567; H01M 10/0569
See application file for complete search history.

(56) References Cited

U.S. PATENT DOCUMENTS

| 2010/0081062 | A1 | 4/2010 | Chiga et al. |
| 2015/0147644 | A1 | 5/2015 | Kinoshita et al. |
| 2016/0190585 | A1* | 6/2016 | Yoon ..................... H01M 4/505 429/231.5 |
| 2017/0317380 | A1 | 11/2017 | Takijiri et al. |

FOREIGN PATENT DOCUMENTS

| JP | 2004-111257 A | 4/2004 |
| JP | 2015-128044 A | 7/2015 |
| JP | 2016-27530 A | 2/2016 |
| JP | 2016-127024 A | 7/2016 |
| WO | 2008/102493 A1 | 8/2008 |
| WO | 2016/103657 A1 | 6/2016 |
| WO | 2016/151983 A1 | 9/2016 |

OTHER PUBLICATIONS

Translation of International Search Report dated Feb. 27, 2018, issued in counterpart Application No. PCT/JP2017/043909. (2 pages).

* cited by examiner

*Primary Examiner* — Osei K Amponsah
(74) *Attorney, Agent, or Firm* — Westerman, Hattori, Daniels & Adrian, LLP

(57) ABSTRACT

A non-aqueous electrolyte secondary cell provided with: a positive electrode that has a positive electrode active material; a negative electrode; and a non-aqueous electrolyte. The positive electrode active material contains a lithium composite oxide containing Ni, and the non-aqueous electrolyte contains a non-aqueous solvent containing a fluorinated chain carboxylic acid ester and an organochlorine compound. The organochlorine compound is represented by general formula $CF_3CH_2CO\text{---}CClR_1R_2$ (where in the formula, $R_1$ and $R_2$ are respectively independent, and are selected from a hydrogen, a halogen, a C1-2 alkyl group, or a C1-2 halogenated alkyl group).

6 Claims, No Drawings

US 11,201,355 B2

NONAQUEOUS ELECTROLYTE SECONDARY BATTERY

TECHNICAL FIELD

The present invention relates to a technique of a non-aqueous electrolyte secondary battery.

BACKGROUND ART

As a secondary battery having a high output and a high energy density that has been widely used recently, there is known a non-aqueous electrolyte secondary including a positive electrode, a negative electrode, and a non-aqueous electrolyte, wherein the battery is charged/discharged through the movement of lithium ions between the positive electrode and the negative electrode.

Patent Literature 1, for example, discloses a non-aqueous electrolyte secondary battery that includes a positive electrode, a negative electrode, and a non-aqueous electrolyte including a fluorinated chain carboxylate ester. Patent Literature 1 discloses that good charging/discharging efficiency and charging/discharging cyclic characteristics can be provided by using a non-aqueous electrolyte including a fluorinated chain carboxylate ester.

CITATION LIST

Patent Literature

Patent Literature 1: WO2008/102493

SUMMARY

A positive electrode includes a positive electrode active material including a lithium composite oxide. A Ni-containing lithium composite oxide has been conventionally used as the lithium composite oxide for the purpose for example, of improving the charging/discharging capacity of a non-aqueous electrolyte secondary battery.

However, when a non-aqueous electrolyte including a fluorinated chain carboxylate ester as described in Patent Literature 1 is used in a non-aqueous electrolyte secondary battery that includes a positive electrode active material including a Ni-containing lithium composite oxide, the DC resistance (DC-IR) of non-aqueous electrolyte secondary battery may be increased to thereby impair the output characteristics of the non-aqueous electrolyte secondary.

Therefore, it is an advantage of the present disclosure to provide a non-aqueous electrolyte secondary battery that includes a positive electrode active material including a Ni-containing lithium composite oxide and a non-aqueous electrolyte including a fluorinated chain carboxylate ester and can prevent the increase in tire DC resistance of the non-aqueous electrolyte secondary battery.

The non-aqueous electrolyte secondary battery according to one aspect of the present disclosure comprises: a positive electrode comprising a positive electrode active material; a negative electrode; and a non-aqueous electrolyte. Tire positive electrode active material comprises a Ni-containing lithium composite oxide, and the non-aqueous electrolyte comprises a non-aqueous solvent comprising a fluorinated chain carboxylate ester, and an organic chlorine compound. The organic chlorine compound is represented by the general formula: $CF_3CH_2CO-CClR_1R_2$, wherein $R_1$ and $R_2$ are each independently selected from hydrogen, halogen, an alkyl group having 1 to 2 carbon atoms, and a halogenated alkyl group having 1 to 2 carbon atoms.

The increase in the DC resistance of a non-aqueous electrolyte secondary battery can be prevented in a non-aqueous electrolyte secondary battery that includes a positive electrode active material including a Ni-containing lithium composite oxide and a non-aqueous electrolyte including a fluorinated chain carboxylate ester.

DESCRIPTION OF EMBODIMENTS (Basic Findings for Present Disclosure)

A Ni-containing lithium composite oxide can be obtained by, for example, firing a starting material mixture including a Li stalling material and a Ni starting material. However, the firing temperature for the starting material mixture is generally lower than the firing temperature for a stalling material mixture to produce a Ni-free lithium composite oxide, and therefore, the intended Ni-containing lithium composite oxide may not be obtained if the Li starting material or the like is not added in an excessive amount. Thus, a part of the starting materials are likely to remain as unreacted components in the Ni-containing lithium composite oxide obtained. The unreacted components are mainly alkali components such as LiOH and $LiCO_3$, which are Li stalling materials.

When charge/discharge is carried out on a non-aqueous electrolyte secondary battery that includes a positive electrode active material including a Ni-containing lithium composite oxide and a non-aqueous electrolyte including a fluorinated chain carboxylate ester, the fluorinated chain carboxylate ester is decomposed by the alkali components mentioned above, and thus a film derived from the fluorinated chain carboxylate ester is formed on the positive electrode active material. It is considered that the film derived from the fluorinated chain carboxylate ester formed on the positive electrode active material serves as a resistance component that hinders the intercalation and deintercalation of lithium ions to the positive electrode active material because the lithium ion permeability of the film is low, and therefore considered that the DC resistance of the non-aqueous electrolyte secondary battery thus increases.

Then, as a result of the earnest studies, the present inventors have found that an organic chlorine compound is useful as a substance for preventing the generation of the film derived from the fluorinated chain carboxylate ester and therefor preventing the increase in the DC resistance of the non-aqueous electrolyte secondary battery, the organic chlorine compound being represented by the general formula: $CF_3CH_2CO-CClR_1R_2$, wherein $R_1$ and $R_2$ are each independently selected from hydrogen, halogen, an alkyl group having 1 to 2 carbon atoms, and a halogenated alkyl group having 1 to 2 carbon atoms, and they have thus conceived a non-aqueous electrolyte secondary battery of the aspect described below. Herein, the organic chlorine compound represented by the general formula: $CF_3CH_2CO-CClR_1R_2$, wherein $R_1$ and $R_2$ are each independently selected from hydrogen, halogen, an alkyl group having 1 to 2 carbon atoms, and a halogenated alkyl group having 1 to 2 carbon atoms, may sometimes referred to as the first compound.

The non-aqueous electrolyte secondary battery according to one aspect of the present disclosure comprises: a positive electrode comprising a positive electrode active material; a negative electrode; and a non-aqueous electrolyte. The positive electrode active material comprises a Ni-containing lithium composite oxide. The non-aqueous electrolyte comprises a non-aqueous solvent comprising a fluorinated chain carboxylate ester, and an organic chlorine compound. The organic chlorine compound is represented by the general formula: $CF_3CH_2CO-CClR_1R_2$, wherein $R_1$ and $R_2$ are each independently selected from hydrogen, halogen, an alkyl group having 1 to 2 carbon atoms, and a halogenated alkyl group having 1 to 2 carbon atoms.

It is considered that the organic chlorine compound included in the non-aqueous electrolyte of the non-aqueous electrolyte secondary battery according to one aspect of the present disclosure has higher reactivity to the alkali components that contaminates the positive electrode active material than the fluorinated chain carboxylate ester and therefore reacts with the alkali components, and that the reaction between the alkali components and the fluorinated chain carboxylate ester is thus prevented. It is considered that as a result, the formation of the film derived from the fluorinated chain carboxylate ester is prevented on the positive electrode active material.

It is considered that the organic chlorine compound is decomposed by the alkali components as shown in reaction formula (1) below, and that a film composed of the compounds of structural formulae (A) and (B) shown in reaction formula (1) and other compounds (hereinafter referred to as a film derived from the organic chlorine compound) is formed on the surface of the positive electrode active material.

[Formula 1]

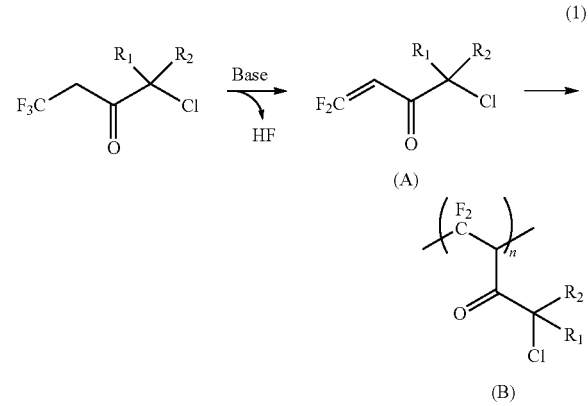

The film derived from the organic chlorine compound and composed of the compounds of structural formulae (A) and (B) above and other compounds include Cl. Cl is likely to draw lithium ions because of its higher electronegativity, whereas the interaction between Cl and lithium is small because of a larger atomic radius of Cl than that of lithium. In other words, it is considered that in the charging/discharging process of a non-aqueous electrolyte secondary battery, lithium ions are drawn to Cl in the film derived from the organic chlorine compound bin not bonded to Cl and that the lithium ions move relatively smoothly in the film derived from the organic chlorine compound. Therefore, it is considered that the film derived from the organic chlorine compound has higher lithium ion permeability than the film derived from a fluorinated chain carboxylate ester, in which Cl is not present. In other words, it is considered that in the non-aqueous electrolyte secondary battery according to one aspect of the present disclosure, the formation of the film derived from a fluoridated chain carboxylate ester, winch has a lower ion permeability, is prevented by the organic chlorine compound in the non-aqueous electrolyte, and that the formation of the film derived from the organic chlorine compound, which has a higher ion permeability, is promoted to thereby prevent the increase in the DC resistance of the non-aqueous electrolyte secondary battery.

The non-aqueous electrolyte secondary battery according to another aspect of the present disclosure comprises a positive electrode comprising a positive electrode active material; a negative electrode; and a non-aqueous electrolyte. The positive electrode active material comprises a Ni-containing lithium composite oxide, and the non-aqueous electrolyte comprises a non-aqueous solvent comprising a fluorinated chain carboxylate ester, and 2-chloro-1,1,1,3-tetrafluoropentane ($CF3-CHCl-CHF-CH2-CH3$). 2-Chloro-1,1,1,3-tetrafluoropentane is an organic chlorine compound. A film derived from an organic chlorine compound containing Cl is formed on the surface of the positive electrode active material also when 2-chloro-1,1,1,3-tetrafluoropentane is included in the non-aqueous electrolyte. According to the non-aqueous electrolyte secondary battery according to the other aspect of the present disclosure, the increase in the DC resistance of the non-aqueous electrolyte secondary battery can be prevented in the non-aqueous electrolyte secondary battery that includes a positive electrode active material including a Ni-containing lithium composite oxide and a non-aqueous electrolyte including a fluorinated chain carboxylate ester.

An embodiment of the non-aqueous electrolyte secondary battery according to one aspect of the present embodiment will be described below in detail. The embodiment described below is illustrative, and the present disclosure is not limited thereto.

The exemplary non-aqueous electrolyte secondary battery according to the present embodiment includes a positive electrode, a negative electrode, and a non-aqueous electrolyte. A separator is preferably provided between the positive electrode and the negative electrode. Specifically, the non-aqueous electrolyte secondary battery has a structure in which an electrode assembly and the non-aqueous electrolyte are housed in an exterior body, the electrode assembly having a wound structure in which the positive electrode and the negative electrode are wound together with the separator interposed therebetween. The electrode assembly is not limited to those having a wound structure, and an electrode assembly in another form may be used, including an electrode assembly having a laminated structure in which positive electrodes and negative electrodes are laminated with separators interposed therebetween. The form of the non-aqueous electrolyte secondary battery is not particularly limited, and examples thereof include a cylindrical shape, a rectangular shape, a coin shape, a button shape, and a laminate.

The non-aqueous electrolyte, the positive electrode, the negative electrode, and the separator used in the exemplary non-aqueous electrolyte secondary battery according to the embodiment will be described in detail below.

[Non-Aqueous Electrolyte]

The non-aqueous electrolyte includes: a non-aqueous solvent including a fluorinated chain carboxylate ester; an organic chlorine compound; and an electrolyte salt. The non-aqueous electrolyte is not limited to a liquid electrolyte (non-aqueous electrolyte solution), and may be a solid electrolyte using a polymer gel or the like.

The fluorinated chain carboxylate ester included in the non-aqueous solvent is not particularly limited as long as it is a compound obtained by replacing at least one hydrogen atom of a chain carboxylate ester with a fluorine atom. In view of, for example, preventing the deterioration in the charging/discharging cyclic characteristics of the non-aqueous electrolyte secondary battery, the fluorinated chain carboxylate ester preferably includes a fluorinated chain carboxylate ester represented by the general formula below:

$R_1—CH_2—COO—R_2$ wherein $R_1$ represents hydrogen or an alkyl group; $R_2$ represents an alkyl group; the total number of the carbon atoms of $R_1$ and $R_2$ is 3 or less; when $R_1$ represents hydrogen, at least part of hydrogen in $R_2$ is replaced with fluorine; and when $R_1$ represents an alkyl group, at least part of hydrogen of at least one of $R_1$ and $R_2$ is replaced with fluorine.

Specifically, at least one selected from, for example, methyl 3,3,3-trifluoropropionate, 2,2,2-trifluoroethyl acetate, methyl 2,3,3,3-tetrafluoropropionate, and methyl 2,3,3-trifluoropropionate can be used as the fluorinated chain carboxylate ester. In view of, for example, preventing the deterioration in the charging/discharging cyclic characteristics of the non-aqueous electrolyte secondary battery, the fluorinated chain carboxylate ester preferably includes 2,2,2-trifluoroethyl acetate ($CH_3CO—OCH_2CF_3$), and more preferably includes 2,2,2-trifluoroethyl acetate ($CH_3CO—OCH_2CF_3$) and methyl 3,3,3-trifluoropropionate ($CF_3CH_2CO—OCH_3$). Since 2,2,2-trifluoroethyl acetate ($CH_3CO—OCH_2CF_3$) and methyl 3,3,3-trifluoropropionate ($CF_3CH_2CO—OCH_2CH_3$) are isomers having the same molecular weight, the structures thereof are similar to each other, and therefore, the reactivities thereof are also similar to each other. Since these compounds including an organic chlorine compound of the general formula: $CF_3CH_2CO—CClR_1R_2$ all have a $CF_3CH_2$ group, these show a smaller steric repulsion for each other than for other molecules having no $CF_3CH_2$ group. It is considered that when these molecules coexist, the fluorinated chain carboxylate ester is easily involved in the reaction for the film formation that starts from the organic chlorine compound of the general formula: $CF_3CH_2CO—CClR_1R_2$, and that a dense film is thus formed. It is also considered that a trim formed when 2,2,2-trifluoroethyl acetate and methyl 3,3,3-trifluoropropionate are included in the non-aqueous electrolyte is denser than that formed when methyl 3,3,3-trifluoropropionate is not included in the non-aqueous electrolyte.

For example, tire content of the fluorinated chain carboxylate ester is preferably 30 vol % or more, more preferably 50 vol % or more and 90 vol % or less, based on the total amount of the non-aqueous solvent. If the content of the fluorinated chain carboxylate ester is less than 30 vol % based on the total amount of the non-aqueous solvent, deterioration in the charging/discharging cyclic characteristics of the non-aqueous electrolyte secondary battery may not be prevented sufficiently compared to the case where the content is within the range described above. When the fluorinated chain carboxylate ester includes 2,2,2-trifluoroethyl acetate, the content of 2,2,2-trifluoroethyl acetate is preferably 30 vol % or more and 90 vol % or less based on the total amount of the non-aqueous solvent, for example. If the content of the 2,2,2-trifluoroethyl acetate is less than 30 vol % based on the total amount of the non-aqueous solvent, deterioration in the charging/discharging cyclic characteristics of the non-aqueous electrolyte secondary battery may not be prevented sufficiently compared to the case where the content is within the range described above.

In addition to the fluorinated chain carboxylate ester, the non-aqueous solvent may include another non-aqueous solvent. As the other non-aqueous solvent, at least one non-aqueous solvent can be used that is selected from cyclic carbonate esters, such as ethylene carbonate, propylene carbonate, and butylene carbonate; chain carbonate esters, such as dimethyl carbonate, diethyl carbonate, and methyl ethyl carbonate; carboxylate esters, such as methyl acetate and ethyl acetate: cyclic ethers, such as 1,3-dioxolane and tetrahydrofuran; linear ethers, such as 1,2-dimethoxyethane and diethyl ether; nitriles, such as acetonitrile; and amides such as dimethylformamide.

The organic chlorine compound included in the non-aqueous electrolyte is represented by the general formula: $CF_3CH_2CO—CClR_1R_2$, wherein $R_1$ and $R_2$ are each independently selected from hydrogen, halogen, an alkyl group having 1 to 2 carbon atoms, and a halogenated alkyl group having 1 to 2 carbon atoms. As the organic chlorine compound, at least one organic chlorine compound can be used that is selected from, for example, 1-chloro-1,4,4,4-tetrafluorobutan-2-one, 1-choro-4,4,4-tetrafluorobutan-2-one, 4-chloro-1,1,1-trifluoropentan-3-one. In view of, for example, reducing the DC resistance of the non-aqueous electrolyte secondary battery, the organic chlorine compound preferably includes 1-chloro-1,4,4,4-tetrafluorobutan-2-one.

The organic chlorine compound included in the non-aqueous electrolyte may include both of a compound represented by the general formula: $CF_3CH_2CO—CClR_1R_2$ and 2-chloro-1,1,1,3-tetrafluoropentane, wherein $R_1$ and $R_2$ are each independently selected from hydrogen, halogen, an alkyl group having 1 to 2 carbon atoms, and a halogenated alkyl group having 1 to 2 carbon atoms.

For example, the content of the organic chlorine compound is preferably 0.002 mass % or more and 0.1 mass % or less, more preferably 0.01 mass % or more and 0.05 mass % or less, based on the total amount of the non-aqueous electrolyte. If the content of the organic chlorine compound is less than 0.002 mass % based on the total amount of the non-aqueous electrolyte, the formation of the film derived from the fluorinated chain carboxylate ester may not be prevented sufficiently and the DC resistance of the non-aqueous electrolyte secondary battery may thus increase, compared to the case where the content is within the range described above. If the content of the organic chlorine compound is more than 0.1 mass % based on the total amount of the non-aqueous electrolyte, a film derived from the organic chlorine compound may be formed on the negative electrode to thereby decrease the capacity compared to the case where the content is within the range described above.

The electrolyte salt included in the non-aqueous electrolyte is preferably a lithium salt. As the lithium salt, those generally used as a supporting electrolyte for conventional non-aqueous electrolyte secondary batteries can be used. Specific examples thereof include $LiPF_6$, $LiBF_4$, $LiAsF_6$, $LiClO_4$, $LiCF_3SO_3$, $LiN(FSO_2)_2$, $LiN(C_lF_{2l+1}SO_2)(C_mF_{2m+1}SO_2)$ (where l and m are each an integer of 1 or more). $LiC(C_pF_{2p+1}SO_2)(C_qF_{2q+1}SO_2)(C_rF_{2r+1}SO_2)$ (where p, q and r are each an integer of 1 or more), $Li[B(C_2O_4)_2]$ (lithium bis(oxalate)borate (LiBOB)), $Li[B(C_2O_4)F_2]$, $Li[P(C_2O_4)F_4]$, and $Li[P(C_2O_4)_2F_2]$. These lithium salts may be used singly or in combinations of two or more thereof.

[Positive Electrode]

The positive electrode includes, tor example, a positive electrode collector such as metal foil and a positive electrode active material layer formed on the positive electrode collector. Foil of a metal, such as aluminum, that is stable in the electric potential range of the positive electrode, a film with such a metal disposed as an outer layer, and the like can be used for the positive electrode collector. The positive electrode active material layer includes, for example, a positive electrode active material, a binder, an electrical conductor, and other components.

The positive electrode can be produced by, for example, applying a positive electrode mixture slurry containing the positive electrode active material, the binder, the electrical conductor, and other components to the positive electrode collector, drying the applied slurry to thereby form a positive electrode active material layer on the positive electrode collector, and rolling the positive electrode active material layer.

The positive electrode active material includes a Ni-containing lithium composite oxide. The Ni-containing lithium composite oxide is not particularly limited, and at least one lithium composite oxide can be used that is selected from, tor example, a Li—Ni composite oxide, a Li—Ni—Co composite oxide, a Li—Ni—Mn—Co composite oxide, a Li—Ni—Co-M composite oxide, and a Li—Ni—Mn—Co-M composite oxide. Among these, a Li—Ni composite oxide and a Li—Ni—Co composite oxide are preferable, for example. M is not particularly limited as long as it is at least one element other than Li, Ni, or Co. M may be at least one element selected from, for example, Al, Mg, Ti, Cr, Cu, Ze, Sn, Zr, Nb, Mo, Ta, W, Na, K, Ba, Sr, Bi, Be, Mn, and B.

The Ni-containing lithium composite oxide preferably has a Ni content of 20 mol % or more, preferably 50 mol % or more, based on the total molar amount of metal elements other than lithium in the lithium composite oxide. If the Ni content is less than 20 mol % based on the total molar amount of the metal elements other than lithium in the lithium composite oxide, the charging-discharging capacity of the non-aqueous electrolyte secondary battery may be decrease compared to the case where the content is within the range described above.

The Ni-containing lithium composite oxide preferably contain Co in view of, for example, the stability of the crystal structure, and the Co content is preferably 1 mol % or more and 20 mol % or less, more preferably 5 mol % or more and 15 mol % or less, based on the total molar amount of metal elements other than lithium in the lithium composite oxide. If the Co content is less than 1 mol % based on the total molar amount of the metal elements other than lithium in the lithium composite oxide, the crystal structure may be unstable to thereby impair the charging discharging characteristics compared to the case where the content is within the range described above. If the Co content is more than 20 mol % based on the total molar amount of the metal elements other than lithium in the lithium composite oxide, the charging/discharging capacity of the non-aqueous electrolyte secondary battery may be decreased compared to the case where the content is within the range described above.

The content of each element in the Ni-containing lithium composite oxide can be determined with, for example, an inductively coupled plasma atomic emission spectrometry (ICP-AES), an electron probe microanalyzer (EPMA), or an energy dispersive X-ray analyzer (EDX).

The content of the Ni-containing lithium composite oxide is preferably 50 mass % or more, more preferably 80 mass % or more, based on the total amount of the positive electrode active material. If the content of the Ni-containing lithium composite oxide is less than 50 mass % based on the total amount of the positive electrode active material, the charging/discharging capacity of the non-aqueous electrolyte secondary battery may be decrease compared to the case where the content is within the range described above.

An exemplary method for producing the Ni-containing lithium composite oxide is described. For example, a starting material mixture obtained by mixing a Li stalling material, such as LiOH or $LiCO_3$, and a Ni-containing transition metal oxide in a predetermined mixing ratio is fired at a predetermined temperature. For example, the firing temperature is preferably 650° C. or more and 900° C. or less, particularly preferably 700° C. to 850° C. This firing temperature range is lower than the general firing temperature for producing a Ni-free lithium composite oxide, and therefore, the intended Ni-containing lithium composite oxide may not be obtained if the Li starting material or another component is added in an excessive amount. The Li starting material is added such that the molar ratio of Li to the metals other than Li in the mixture is preferably 1.03 or more, more preferably 1.05 or more. If the ratio of Li in the mixture is less than 1.03, the intended Ni-containing lithium composite oxide may not be obtained.

The positive electrode active material may include a Ni-tree lithium composite oxide in addition to the Ni-containing lithium composite oxide. Examples of the Ni-free lithium composite oxide include, but not limited to, a Li—Co composite oxide and a Li—Co-M composite oxide, wherein M represents at least one doped metal elements selected from, for example, Al, Mg, Ti, Cr, Cu, Ze, Sn, Zr, Nb, Mo, Ta, W, Na, K, Ba, Sr, Bi, Be, Mn, and B. These may be used singly or in combinations of two or more thereof.

Examples of the electrical conductor include carbon powders such as carbon black, acetylene black, Ketjenblack, and graphite. These may be used singly or in combinations of two or more thereof.

Examples of the binder include a fluorinated polymer and a rubber polymer. Examples of the fluorinated polymer include polytetrafluoroethylene (PTFE), poly (vinylidene fluoride) (PVdF), and modified products thereof, and examples of the rubber polymer include an ethylene/propylene-isoprene copolymer and an ethylene/propylene/butadiene copolymer. These may be used singly or in combinations of two or more thereof.

[Negative Electrode]

The negative electrode includes, for example, a negative electrode collector such as a metal foil and a negative electrode active material layer formed on the negative electrode collector. Foil of a metal, such as copper, that is stable in the electric potential range of the negative electrode, a film with such a metal disposed as an outer layer, and the like can be used for the negative electrode collector. The negative electrode active material layer includes, for example, a negative electrode active material, a binder, a thickener, and oilier components.

The negative electrode can be produced by, for example, applying to the negative electrode collector a negative electrode mixture slurry containing the negative electrode active material, the thickener, and the binder, and drying the applied slurry to thereby form a negative electrode active material layer on the negative electrode collector, and rolling the negative electrode active material layer.

The negative electrode active material is not particularly limited as long as it is a material that can intercalate and deintercalate lithium ions. Examples thereof include metallic lithium; lithium alloys such as a lithium-aluminum alloy, a lithium-lead alloy, a lithium-silicon alloy, and a lithium-tin alloy; carbon materials such as graphite, coke, fired organic materials; and metal oxides such as $SnO_2$, SnO, and $TiO_2$. These may be used singly or in combinations of two or more thereof.

As the binder, a fluorinated polymer, a rubber polymer, or the like can be used as in the case of the positive electrode, and a styrene/butadiene copolymer (SBR) or the modified product thereof may also be used.

Examples of the thickener include carboxymethylcellulose (CMC) and polyethylene oxide (PEO). These may be used singly or in combinations of two or more.

[Separator]

An ion-permeable and insulating porous sheet is used as the separator, for example. Specific examples of the porous sheet include a microporous thin film, woven fabric, and nonwoven fabric. Suitable examples of the material for the separator include olefin resins such as polyethylene and polypropylene, and cellulose. The separator may be a laminate including a cellulose fiber layer and a layer of fibers of a thermoplastic resin such as an olefin resin. The separator may be a multi-layered separator including a polyethylene layer and a polypropylene layer, and a separator a surface of which is coated with a material suck as an aramid resin or ceramic may also be used as the separator.

EXAMPLES

The present disclosure will be farther described by way of Example below, but is not limited thereto.

Example

[Production of Positive Electrode]

A nickel/cobalt/aluminum composite hydroxide represented by $Ni_{0.82}Co_{0.15}Al_{0.03}(OH)_2$ obtained by coprecipitation was heat-treated to obtain an oxide, and LiOH and the oxide were mixed in a molar ratio of Li to the total metals other than Li of 1.1:1. The mixture was heat-treated at 760° C. for 20 hours in an oxygen atmosphere to obtain a lithium/nickel/cobalt/aluminum composite oxide represented by $LiNi_{0.82}Co_{0.15}Al_{0.03}O_2$(NCA). This was used as a positive electrode active material. The positive electrode active material, acetylene black as an electrical conductor, and polyvinylidene fluoride as a binder were mixed in a mass ratio of 300:1:0.9, and N-methyl-2-pyrrolidone (NMP) was added thereto to prepare a positive electrode mixture slurry. Then, the positive electrode mixture slurry was applied to both sides of aluminum foil as a positive electrode collector. The resulting coating was dried and then rolled with a roller to prepare a positive electrode having a positive electrode active material layer formed on each side of the positive electrode collector. The bulk density of the positive electrode active material was 3.6 g/cm³.

[Production of Negative Electrode]

Artificial graphite as a negative electrode active material, sodium carboxymethylcellulose as a thickener, and a styrene/butadiene copolymer as a binder were mixed in a mass ratio of 100:1:1 to prepare a negative electrode mixture stony. Then, the negative electrode mixture slurry was applied to both sides of copper foil as a negative electrode collector. The resulting coaling was dried and then rolled with a roller to prepare a negative electrode having a negative electrode active material layer formed on each side of the negative electrode collector. The bulk density of the negative electrode active material was 1.7 g/cm³.

[Preparation of Non-aqueous Electrolyte]

In a mixed solvent consisting of fluorinated ethylene carbonate (FEC), propylene carbonate (PC), methyl 3,3,3-trifluoropropionate (FMP), and 2,2,2-trifluoroethyl acetate (FEA) mixed in a volume ratio of 15:5:40:40, lithium hexafluorophosphate ($LiPF_6$) was dissolved at a concentration of 1.3 mol/L to prepare an electrolyte. To 100 parts by mass of the electrolyte, 1.5 parts by mass (1.5 mass %) of vinylene carbonate (VC) and 0.015 parts by mass (0.014 mass %) of 1-chloro-1,4,4,4-tetrafluorobutan-2-one (CTFB: $CF_3CH_2CO$—CClHF) were added, and the resultant was used as the non-aqueous electrolyte for Example.

[Production of Battery]

A lead terminal was attached to each of the positive electrode (30×40 mm) and the negative electrode (32×42 mm). Then, an electrode assembly was produced in which the positive electrode and the negative electrode were faced to each other with a separator therebetween. The electrode assembly was housed with the non-aqueous electrolyte in a laminated exterior container made of aluminum to produce a non-aqueous electrolyte secondary battery having a design capacity of 50 mAh. Constant-current charge at 0.5 It (25 mA) was carried out on the non-aqueous electrolyte secondary battery produced to a voltage of 4.35 V. Next, constant-voltage charge was carried out on the battery at a constant voltage of 4.35 V to a current of 0.05 It (2.5 mA), followed by a rest for 20 minutes. Then, constant-current discharge at 0.5 It (25 mA) was carried out on the battery to a voltage of 2.5 V. Such a charging/discharging cycle was carried out twice to stabilize the battery. The battery thus obtained was used as a battery of Example.

Comparative Example

A non-aqueous electrolyte was produced in the same manner as in Example, except that 1-chloro-1,4,4,4-tetrafluorobutan-2-one (CTFB: $CF_3CH_2CO$—CClHF) was not added in the production of the non-aqueous electrolyte. A battery was produced in the same manner as in Example, except that this was used as a non-aqueous electrolyte for Comparative Example.

[Determination of Initial Capacity]

In a thermostatic chamber at 25° C. constant-current charge at 0.2 It (10 mA) was carried out on each of batteries of Example and Comparative Example to a voltage of 4.2 V. Next, constant-voltage charge was carried out thereon at a constant voltage of 4.2 V to a current of 0.2 It (1 mA), followed by a rest for 20 minutes. Then, constant-current discharge at 0.2 It (650 mA) was carried out thereon to a voltage of 3.0 V. and the discharge capacity at this time was taken as the initial discharge capacity. The initial capacity of the batteries of Example and Comparative Example was calculated by the following equation.

Initial capacity (mAh/g)=Initial discharge capacity (mAh)/Weight of positive electrode active material (g)

[Determination of DC Resistance (DC-IR)]

In a thermostatic chamber at 25° C., constant-current charge at 0.2 It (10 mA) was carried out on each of batteries of Example and Comparative Example to a voltage of 4.2 V. The voltage at this time is designated as $V_0$. Next, constant-current discharge at 0.2 It (10 mA) was carried out thereon for 1 minute. The voltage after 1 minute at this time is designated as $V_1$. DC-IR was determined by the following equation.

$$DC\text{-}IR=(V_0-V_1)/10 \text{ mA}$$

[Determination of Capacity Retention Rate]

In a thermostatic chamber at 25° C. constant-current charge at 0.2 It (10 mA) was carried out on each of batteries of Example and Comparative Example to a voltage of 4.2 V. Next, constant-voltage charge was carried out thereon at a constant voltage of 4.2 V to a current of 0.02 It (1 mA), followed by a rest for 20 minutes. Then, constant-current discharge at 0.2 It (650 mA) was carried out thereon to a voltage of 3.0 V. Such a charging/discharging cycle was repetitively carried out 300 tunes on each of batteries. The capacity retention rate was determined by the following equation.

Capacity Retention Rate=(Discharge Capacity at 300th Cycle/Discharge Capacity at First Cycle)×100

Table 1 shows the positive electrode active material, the formulation of the non-aqueous solvent, and the presence or absence of 1-chloro-1,4,4,4-tetrafluorobutan-2-one used in the batteries of Example and Comparative Example, as well as the results of the initial capacity, the DC resistance (DC-IR), and the capacity retention rate of the batteries of Example and Comparative Example. As for the DC resistance in Table 1, the DC resistance of the battery of Example is shown relatively to that of Comparative Example, which was taken as the basis (100%), and as for the capacity retention rate in Table 1, the capacity retention rate of the battery of Example is shown relatively to that of Comparative Example, which was taken as the basis (100%).

having 1 to 2 carbon atoms, and a halogenated alkyl group having 1 to 2 carbon atoms.

Reference Example 1

LiOH and cobalt hydroxide were mixed in a molar ratio of Li to Co of 1:1, and the mixture was heat-treated at 950° C. for 20 hours in an oxygen atmosphere to thereby obtain a lithium/cobalt composite oxide represented by $LiCoO_2$ (LCO). A battery was produced in the same manner as in example, except that tins composite oxide was used as a positive electrode active material for Reference Example 1.

Reference Example 2

LiOH and cobalt hydroxide were mixed in a molar ratio of Li to Co of 1:1, and the mixture was heat-treated at 950° C. for 20 hours in an oxygen atmosphere to thereby obtain a lithium/cobalt composite oxide represented by $LiCoO_2$ (LCO). This was used as a positive electrode active material for Reference Example 2. A non-aqueous electrolyte was produced in the same manner as in Example, except that 1-chloro-1,4,4,4-tetrafluorobutan-2-one (CTFB: $CF_3CH_2CO$—CClHF) was not added in the production of the non-aqueous electrolyte. This was used as a non-aqueous electrolyte for Reference Example 2. A battery was produced in the same manner as in Example, except that these positive electrode active material and non-aqueous electrolyte were used.

The initial capacity, the DC resistance (DC-IR), and the capacity retention rate of the batteries of Reference Examples 1 and 2 were determined under the same conditions described above.

TABLE 1

| | Positive Electrode Active Material | Formulation of Non-Aqueous Solvent (Volume Ratio) | Addition of CTFB | DC Resistance (DC-IR) | Initial Capacity (mAh/g) | Capacity Retention Rate |
|---|---|---|---|---|---|---|
| Example | NCA | FEC/PC/FMP/FEA (15/5/40/40) | yes | 79% | 193 | 100% |
| Comparative Example | NCA | FEC/PC/FMP/FEA (15/5/40/40) | no | 100% | 193 | 100% |

NCA: $LiNi_{0.82}Co_{0.15}Al_{0.03}O_2$
FEC: Fluorinated Ethylene Carbonate,
PC: Propylene Carbonate,
FMP: Methyl 3,3,3-Trifluoropropionate,
FEA: 2,2,2-Trifluoroethyl Acetate,
CTFB: 1-Chloro-1,4,4,4-tetrafluorobutan-2-one The battery of Example had a comparable performance in terms of the initial capacity and the capacity retention rate to that of Comparative Example, but had a lower DC resistance than that of Comparative Example. In other words, in a non-aqueous electrolyte secondary battery in which a positive electrode active material including a Ni-containing lithium composite oxide and a non-aqueous electrolyte including a fluorinated chain carboxylate ester are used as in the battery of Example, the increase in the DC resistance of the non-aqueous electrolyte secondary battery can be prevented by adding to the non-aqueous electrolyte an organic chlorine compound represented by the general formula: $CF_3CH_2CO$—$CClR_1R_2$, wherein $R_1$ and $R_2$ are each independently selected from hydrogen, halogen, an alkyl group Table 2 shows the positive electrode active material, the formulation of the non-aqueous solvent, and the presence or absence of 1-chloro-1,4,4,4-tetrafluorobutan-2-one used in the batteries of Reference Examples 1 and 2, as well as the results of the initial capacity, the DC resistance (DC-IR), and the capacity retention rate of the batteries of Reference Examples 1 and 2. As for the DC resistance in Table 2, the DC resistance of each of the batteries of Reference Examples 1 and 2 is shown relatively to that of Comparative Example, which was taken as the basis (100%), and as for the capacity retention rate in Table 2, the capacity retention rate of each of the batteries of Reference Examples 1 and 2 is shown relatively to that of Comparative Example, which was taken as the basis (100%).

TABLE 2

| | Positive Electrode Active Material | Formulation of Non-Aqueous Solvent (Volume Ratio) | Addition of CTFB | DC Resistance (DC-IR) | Initial Capacity (mAh/g) | Capacity Retention Rate |
|---|---|---|---|---|---|---|
| Reference Example 1 | LCO | FEC/PC/FMP/FEA (15/5/40/40) | yes | 114% | 141 | 99% |
| Reference Example 2 | LCO | FEC/PC/FMP/FEA (15/5/40/40) | no | 115% | 142 | 100% |

LCO: $LiCoO_2$
FEC: Fluorinated Ethylene Carbonate,
PC: Propylene Carbonate,
FMP: Methyl 3,3,3-Trifluoropropionate,
FEA: 2,2,2-Trifluoroethyl Acetate,
CTFB: 1-Chloro-1,4,4,4-tetrafluorobutan-2-one In the comparison between the batteries of Reference Examples 1 and 2, there was almost no difference between them in the DC resistance, and thus, these batteries had a comparable performance. In other words, it can be said that in a non-aqueous electrolyte secondary battery in which a positive electrode active material including a lithium composite oxide that does not contain Ni or Mn and a non-aqueous electrolyte including a fluorinated chain carboxylate ester are used, the effect of preventing the increase in the DC resistance of the non-aqueous electrolyte secondary battery cannot be exhibited sufficiently even when adding to the non-aqueous electrolyte an organic chlorine compound represented by the general formula: $CF_3CH_2CO$—$CClR_1R_2$, wherein $R_1$ and $R_2$ are each independently selected from hydrogen, halogen, an alkyl group having 1 to 2 carbon atoms, and a halogenated alkyl group having 1 to 2 carbon atoms. It is probably because there is almost no alkali component that is reactive to a fluorinated chain carboxylate ester or the organic chlorine compound above in a positive electrode active material when using a lithium composite oxide that does not contain Ni or Mn. It is considered that the reason why the DC resistance of the batteries of Reference Examples 1 and 2 was higher than that of Comparative Example 1 is due to the performance of the positive electrode active material used.

The invention claimed is:

1. A non-aqueous electrolyte secondary battery comprising: a positive electrode including a positive electrode active material; a negative electrode; and a non-aqueous electrolyte, wherein the positive electrode active material comprises a Ni-containing lithium composite oxide, the non-aqueous electrolyte comprises a non-aqueous solvent including a fluorinated chain carboxylate ester, and an organic chlorine compound, and the organic chlorine compound comprises at least one of a first compound represented by the general formula: $CF_3CH_2CO$—$CClR_1R_2$, and 2-chloro-1,1,1,3-tetrafluoropentane, wherein $R_1$ and $R_2$ are each independently selected from hydrogen, halogen, an alkyl group having 1 to 2 carbon atoms, and a halogenated alkyl group having 1 to 2 carbon atoms.

2. The non-aqueous electrolyte secondary battery according to claim 1, wherein the first compound comprises 1-chloro-1,4,4,4-tetrafluorobutan-2-one.

3. The non-aqueous electrolyte secondary battery according to claim 1, wherein the fluorinated chain carboxylate ester comprises 2,2,2-trifluoroethyl acetate.

4. The non-aqueous electrolyte secondary battery according to claim 1, wherein the fluorinated chain carboxylate ester comprises 2,2,2-trifluoroethyl acetate and methyl 3,3,3-trifluoropropionate.

5. The non-aqueous electrolyte secondary battery according to claim 1, wherein the content of the fluorinated chain carboxylate ester is 30 vol % or more based on the total amount of the non-aqueous solvent.

6. The non-aqueous electrolyte secondary battery according to claim 1, wherein the organic chlorine compound comprises the first compound and 2-chloro-1,1,1,3-tetrafluoropentane.

* * * * *